United States Patent [19]

Terae et al.

[11] Patent Number: 4,465,849

[45] Date of Patent: Aug. 14, 1984

[54] METHOD FOR THE PREPARATION OF AN AQUEOUS EMULSION OF SILICONE

[75] Inventors: Nobuyuki Terae; Akira Abe, both of Gunma, Japan

[73] Assignee: Shin-Etsu Chemical Co., Ltd., Tokyo, Japan

[21] Appl. No.: 524,087

[22] Filed: Aug. 17, 1983

[30] Foreign Application Priority Data

Aug. 19, 1982 [JP] Japan .................... 57-143653

[51] Int. Cl.$^3$ .............................................. C07F 7/08
[52] U.S. Cl. ...................... 556/450; 556/453; 556/455; 556/456; 528/12; 528/20; 528/21
[58] Field of Search ............ 556/450, 453, 456, 455; 528/12, 20, 21

[56] References Cited

U.S. PATENT DOCUMENTS

| | | | |
|---|---|---|---|
| 2,901,460 | 8/1959 | Boldebuck | 556/450 X |
| 3,231,496 | 1/1966 | Pater | 556/456 X |
| 3,364,246 | 1/1968 | Rossmy | 556/450 |
| 3,373,138 | 3/1968 | Brown | 556/450 X |
| 3,489,782 | 1/1970 | Pruvost et al. | 556/456 X |
| 4,066,594 | 1/1978 | Moeller | 556/453 X |

*Primary Examiner*—Paul F. Shaver
*Attorney, Agent, or Firm*—Toren, McGeady and Stanger

[57] ABSTRACT

A very simple and versatile method is proposed for the preparation of an aqueous emulsion of silicone in which an organochlorosilane or a mixture of organochlorosilanes is added dropwise into an aqueous medium in the presence of a surface active agent or, preferably, into an aqueous medium containing a surface active agent in advance followed by or with concurrent removal of the hydrogen chloride from the mixture by adding an alkaline neutralizing agent or by use of the techniques of ion exchange so that a stable aqueous emulsion can be produced in the aqueous medium at the same time as the organochlorosilane or silanes are hydrolyzed followed by the dehydration condensation of the resultant silanol compounds to form an organopolysiloxane in situ by the catalytic activity of the hydrogen chloride formed by the hydrolysis.

11 Claims, No Drawings

METHOD FOR THE PREPARATION OF AN AQUEOUS EMULSION OF SILICONE

BACKGROUND OF THE INVENTION

The present invention relates to a method for the preparation of an aqueous emulsion of silicone, i.e. organopolysiloxane, or, more particularly, to a method for the preparation of an aqueous emulsion of an organopolysiloxane directly starting from organochlorosilanes.

As is well known, silicones or organopolysiloxane compositions are widely used in various fields utilizing their unique properties. When organopolysiloxanes are used as an antifoam agent, mold release agent, water repellent agent, polishing material and the like, the most widely accepted form of the silicone compositions is an aqueous emulsion which is prepared by emulsifying the organopolysiloxane in water in the presence of a surface active agent dissolved in the aqueous medium.

Needless to say, organopolysiloxanes are usually prepared by the hydrolysis of an organochlorosilane or a mixture of organochlorosilanes followed by the dehydration condensation of the silanols formed by the hydrolysis. Therefore, the usually undertaken way for the preparation of an aqueous emulsion of silicone is the secondary emulsifying processing of an organopolysiloxane prepared in advance. Therefore, an aqueous emulsion of silicone is prepared usually in a process including the steps for the hydrolysis of an organochlorosilane or chlorosilanes, dehydration condensation of the hydrolyzate to give an organopolysiloxane, purification of the organopolysiloxane and emulsification of the purified organopolysiloxane in water. Such a long sequence of process steps necessarily requires a high cost for the preparation of the emulsion. In addition, the rheological nature of the organopolysiloxane is limited in order to be satisfactorily emulsified in water. For example, an organopolysiloxane having an excessively high viscosity cannot be emulsified in water without dilution with a suitable organic solvent and resinous organopolysiloxanes can hardly be emulsified in water presenting great drawbacks to the practical application of silicone aqueous emulsions.

As viewed from the other side, organochlorosilanes are usually produced by the so-called direct method in which metallic silicon is reacted with a chlorinated hydrocarbon such as methyl chloride and chlorobenzene. In this case, various organochlorosilanes are concurrently produced while the monoorganotrichlorosilanes are produced in amounts over the industrial consumption thereof in comparison with the organochlorosilanes of the other types so that the monoorganotrichlorosilanes must be discarded as an industrial waste of nuisance. This situation led to a proposal of a method for the effective utilization of an organotrichlorosilane in which such an organotrichlorosilane is first converted into a corresponding trialkoxysilane which is then emulsified in water (see, for example, Japanese Patent Publication No. 52-12219). This method is, however, not always very advantageous from the standpoint of the production cost due to the expensive step of conversion of the trichlorosilane into the trialkoxysilane in addition to the limitation in the selection of the surface active agent used in the emulsification of the trialkoxysilane.

Therefore, it has been eagerly desired to develop an inexpensive method for the preparation of an aqueous emulsion of silicone and, if possible, a method in which hitherto valueless monoorganotrichlorosilanes can be utilized as a starting material for an aqueous emulsion of a silicone composition.

SUMMARY OF THE INVENTION

It is therefore an object of the present invention to provide a novel and very inexpensive method for the preparation of an aqueous emulsion of silicone by omitting one or more of the expensive steps in the conventional methods for the preparation of an aqueous emulsion of silicone.

Another object of the invention is to provide a novel method in which the hitherto valueless monoorganotrichlorosilanes can be effectively utilized as a starting material for the preparation of an aqueous emulsion of silicone.

Thus, the method of the present invention for the preparation of an aqueous emulsion of silicone comprises the steps of:

(a) adding an organochlorosilane or a mixture of organochlorosilanes each expressed by the general formula $R_nSiCl_{4-n}$, in which R is a hydrogen atom or a halogen-substituted or unsubstituted monovalent hydrocarbon group having from 1 to 20 carbon atoms, at least one of the groups R being not a hydrogen atom, and n is a number of 1, 2 or 3, dropwise into an aqueous medium in the presence of a surface active agent under agitation to effect the hydrolysis of the silane or silanes followed by the dehydration condensation of the resultant organosilanols into an organopolysiloxane with simultaneous emulsification of the organopolysiloxane in the aqueous medium to form an aqueous emulsion, and (b) removing the hydrogen chloride formed by the hydrolysis of the silane or silanes from the aqueous emulsion by use of a neutralizing agent.

DETAILED DESCRIPTION OF THE PREFERRED EMBODIMENTS

In view of the above described problems in the prior art for the preparation of an aqueous emulsion of silicone, the inventors have continued extensive investigations for developing a novel method for the preparation of the desired silicone emulsions and arrived at the discovery of the above described method of the present invention. It has been established that the above described inventive method is, even by setting aside the economical advantages, indeed effective for the preparation of an aqueous emulsion of a highly viscous or resinous organopolysiloxanes, which can be emulsified only with extreme difficulties in the prior art methods, can readily be obtained in the form of an aqueous emulsion. Further, the hitherto useless organotrichlorosilanes can be fully utilized as a starting material for the preparation of an aqueous silicone emulsion.

The organochlorosilanes used as the starting material in the inventive method are represented by the above given general formula and the monovalent hydrocarbon group having from 1 to 20 carbon atoms denoted by the symbol R is exemplified by alkyl groups such as methyl, ethyl, propyl and butyl groups, alkenyl groups such as vinyl and allyl groups, aryl groups such as phenyl and tolyl groups and aralkyl groups such as benzyl group. The halogen-, e.g. chlorine-, substituted hydrocarbon groups obtained by the partial substitution of chlorine atoms for the hydrogen atoms in the above named hydrocarbon groups are also suitable.

Following are several examples of the organochlorosilanes suitable for use in the inventive method though not limited thereto: methyl trichlorosilane; dimethyl dichlorosilane; trimethyl chlorosilane; methyl dichlorosilane; dimethyl chlorosilane; diethyl dichlorosilane; di(n-propyl) dichlorosilane; phenyl trichlorosilane; diphenyl chlorosilane; methyl phenyl dichlorosilane; vinyl trichlorosilane; methyl vinyl dichlorosilane; dimethyl vinyl chlorosilane; chloromethyl trichlorosilane; chloromethyl vinyl dichlorosilane; and 3,3,3-trifluoropropyl methyl dichlorosilane. In addition to the above named organochlorosilanes, certain chlorosilanes having no organic groups, such as silicon tetrachloride and trichlorosilane, may be used in combination with the organochlorosilanes though in a limited amount. As is mentioned before, the hydrolysis of the above named organochlorosilane or silanes in an aqueous medium by dropwise addition must be performed in the presence of a surface active agent which may be admixed either with the organochlorosilane or with the aqueous medium. It is of course optional that both of the organochlorosilanes and the aqueous medium contain the surface active agent. A convenient way for having a surface active agent in the reaction system is that the surface active agent is dissolved in the aqueous medium and the organochlorosilane or a mixture of silanes is added dropwise into the surfactant-containing aqueous medium.

The surface active agent is not limited to those of a particular type including nonionic, anionic, cationic and amphoteric ones. It is optional that two kinds or more of surface active agents are used in combination according to need. At any rate, it is advisable that the value of HLB of the surface active agent or the overall value of HLB of the surfactants used in combination is in the range from 5 to 20 or, preferably, from 8 to 18 since no satisfactory aqueous emulsion can be formed with an excessively hydrophilic surface active agent having an HLB value over 20 or with an excessively oleophilic surface active agent having an HLB value smaller than 5.

The amount of the surface active agent to be present in the reaction system should of course be in a suitable range since no satisfactory aqueous emulsion can be formed with a too small amount of the surface active agent while the use of an excessively large amount of the surface active agent is economically undesirable without particular additional advantages. Although dependent on the types of the surface active agent or other factors, the weight ratio of the surface active agent to the organochlorosilane or silanes should be in the range from 0.001 to 2 and, when the surface active agent is dissolved in advance in the aqueous medium, the amount thereof should be in the range from about 1/1000 to about 1/5 of the water.

As is mentioned above, the type of the surface active agent is not particularly limitative and various kinds of known surface active agents may be used. For example, suitable nonionic surface active agents include fatty acid esters of polyhydric compounds such as esters of higher fatty acids with glycerin, glycols, pentaerithritol and sorbitan as well as various kinds of polyoxyethylene condensates, such as higher alcohol condensates, higher fatty acid condensates, higher fatty acid amide condensates, higher alkylamine condensates and alkylphenol condensates, and polypropylene oxide condensates.

Suitable cationic surface active agents include various kinds of salts of primary amines, secondary amines, tertiary amines, imidazole, quaternary alkyl ammonium and quaternary alkyl benzyl ammonium. Further, suitable anionic surface active agents include various kinds of salts of higher fatty acids, higher alkyl dicarboxylates, higher alkyl sulfonic acids, higher alkyl phosphates, sulfuric acid esters of higher fatty acids, sulfonic acid esters of higher fatty acids, alkyl sulfonates of higher fatty acid amides, condensates of higher fatty acids and amino acids, alkylbenzene sulfonic acids and alkylbenzimidazole sulfonic acids and the like.

One of the steps of the inventive method is the hydrolysis of the organochlorosilane or silanes in the presence of the surface active agent which is conveniently performed by adding the chlorosilane or a mixture of chlorosilane dropwise into an aqueous medium containing the surface active agent under agitation. The organochlorosilane is converted by this hydrolysis into a corresponding organosilanol compound which is then condensed by dehydration into an organopolysiloxane by the catalytic activity of the hydrogen chloride formed by the hydrolysis of the chlorosilane. The organopolysiloxane is directly emulsified in the aqueous medium as it is formed when the mixture is vigorously agitated in the presence of the surface active agent. Therefore, the inventive method provides an efficient method for the preparation of an aqueous emulsion of an organopolysiloxane which can hardly be emulsified in the prior art methods such as the organopolysiloxanes derived from the organotrichlorosilanes and obtained only in a gel-like form. This is because the finely dispersed particles of the organosilane triol formed by the hydrolysis of the trichlorosilane in the aqueous medium is protected by the surface active agent and the condensation reaction of the silanol proceeds only within each particle so that formation of a gelled mass never takes place. This advantage is particularly remarkable when a neutralizing agent for the hydrogen chloride, i.e. a basic or alkaline material, is contained in advance in the aqueous medium to reduce the catalytic activity of the hydrogen chloride. Further, aqueous emulsions of silicone can be readily prepared even with a formulation of the organochlorosilanes which necessarily gives an organopolysiloxane of an extremely high viscosity. In this case, the diorganodichlorosilane added to the aqueous medium is first hydrolyzed to form a low-molecular cyclic or linear organopolysiloxane in an emulsified form which is then polycondensed or rearranged by the catalytic activity of the hydrogen chloride formed in the hydrolysis in a manner something like the so-called emulsion polymerization.

The hydrolysis reaction of organochlorosilanes in the aqueous medium necessarily forms hydrogen chloride as a byproduct which should be removed from the aqueous medium at any rate in order that the aqueous emulsion product may have not excessively strong acidity or be desirably neutral. Removal of the hydrogen chloride from the aqueous medium can be performed in several different ways.

When removal of the hydrogen chloride from the aqueous medium is performed subsequent to the completion of the hydrolysis and condensation of the organochlorosilanes, a basic or alkaline compound is added to the emulsion as a neutralizing agent. Suitable basic or alkaline materials are exemplified by the hydroxides, oxides, carbonates, silicates and aluminates of alkali metals such as lithium, sodium and potassium in the form of an aqueous solution, ammonia water, primary, secondary and tertiary amine compounds, urea and derivatives thereof, imide compounds, amide compounds and the like.

The amount of the basic or alkaline neutralizing agent added to the aqueous emulsion should be preferably in the range from 0.8 to 2.0 times of the equivalent amount to the hydrogen chloride to be neutralized since deficiency in the amount of the neutralizing agent naturally results in an unacceptably strong remaining acidity of the emulsion while an excessively large amount of an alkaline material may adversely affect the stability of the resultant aqueous emulsion.

In addition to the above described conventional method of neutralization with a basic or alkaline material, the techniques of ion exchange are also applicable to the neutralization of the acidic aqueous emulsion. Various types of ion exchange materials are suitable for the purpose but a preferable one is a polyamine-type anion exchange resin in the OH-form. The amount of the ion exchange resin is of course not particularly limitative and should be determined according to the type of the ion exchange resin, the acidity of the emulsion, the manner in which the acidic emulsion is contacted with the ion exchange resin and other factors although an excessively large amount of the resin is undesirable due to the possible loss of the emulsion as carried by the resin when the resin is separated from the emulsion while deficiency in the amount of the ion exchange resin naturally results in insufficient neutralization of the acidity. For example, the ion exchange equivalent of the resin should be in the range from 1.0 to 2.0 times of the amount of the hydrogen chloride by moles when the ion exchange resin is added to the aqueous emulsion. Alternatively, the acidic aqueous emulsion may be introduced into a column filled with the ion exchange resin at the top to flow down through the bed of the resin. When such a measure is undertaken to neutralize the acidity, the amount of the ion exchange resin filling the column should have an ion exchange equivalent preferably in the range from 1.0 to 4.0 times by moles of the hydrogen chloride to be neutralized.

As is suggested before, it is also an advantageous way that the hydrolysis of the organochlorosilanes followed by condensation is performed in the presence of the above described neutralizing agent for the hydrogen chloride so that the formation of the emulsified organopolysiloxane and neutrailization of the acidity of the aqueous medium can proceed simultaneously. This way of concurrent hydrolysis of the chlorosilanes and neutralization of the hydrogen chloride is particularly advantageous when a chlorosilane containing a large amount of the hydrolyzable chlorine atoms, such as trichlorosilanes or silicon tetrachloride, is used as the starting silane compound since otherwise premature gelation of the organopolysiloxane may eventually take place due to the excessively strong catalytic activity of the hydrogen chloride. That is, the neutralizing agent may be added in advance to the aqueous medium containing a surface active agent before the addition of the organochlorosilane so that the hydrogen chloride formed by the dropwise addition of the organochlorosilane into the aqueous medium is neutralized as it is formed. Alternatively, the neutralizing agent may be added to the aqueous medium continuously or portionwise to balance the hydrogen chloride formed from the organochlorosilane which is also added dropwise to the aqueous medium. This manner of addition of the basic or alkaline neutralizing agent is advantageous when an excessively strong alkalinity of the aqueous medium, though maybe transient, should be avoided.

The condition of temperature at which the hydrolysis-condensation of the starting chlorosilanes with simultaneous emulsification of the organopolysiloxane is not particularly limitative. Usually, the temperature should be in the range from 5° to 80° C. or, preferably, in the range from 10° to 50° C. It is advisable that the organochlorosilane is added to the aqueous medium bit by bit or slowly under vigorous agitation in order to obtain full emulsification of the organopolysiloxane formed in situ into particles as fine as possible.

The method of the present invention is very versatile in respect of the formulation of the silane mixture to be added into the aqueous medium and various kinds of hydrolyzable or non-hydrolyzable silane compounds may be admixed with the organochlorosilanes represented by the above defined general formula $R_nSiCl_{4-n}$ in order to impart specific properties to the resultant silicone emulsions or the organopolysiloxane compositions. For example, modification of the organopolysiloxane with a so-called carbon-functional organosilane can readily be performed by admixing one or more of such carbon-functional organosilanes with the organochlorosilane or silanes.

Several of the examples of such carbon-functional organosilanes include: vinyl triethoxysilane; vinyl tri(2-methoxyethoxy)silane; 3-glycidyloxypropyl trimethoxysilane; vinyl tri(tert-butyryloxy)silane; 3-methacryloxypropyl trimethoxysilane; 3-N-(2-aminoethyl)aminopropyl trimethoxysilane; 3-N-(2-aminoethyl)aminopropyl methyl dimethoxysilane; 3-chloropropyl trimethoxysilane; 3-mercaptopropyl trimethoxysilane; 3-aminopropyl triethoxysilane; 3-carbamidopropyl triethoxysilane; 2-(3,4-epoxycyclohexyl)ethyl trimethoxysilane; methyl dimethoxy chlorosilane; vinyl ethoxy dichlorosilane; 3-aminopropyl dipropoxy chlorosilane and the like.

In short, the principle of the inventive method is very simple including the hydrolysis of an organochlorosilane in an aqueous medium followed by dehydration condensation of the resultant organosilanol in the presence of a surface active agent and subsequent or concurrent removal of the hydrogen chloride formed by the hydrolysis from the aqueous emulsified mixture of the organopolysiloxane. The inventive method is very advantageous due to the versatility in respect of the types of the organochlorosilanes to give an aqueous silicone emulsion which can hardly be obtained in the prior art methods. The aqueous silicone emulsion obtained by the inventive method can be used in a variety of application fields as wide as for the conventional silicone emulsions such as a water-repellent agent, antifoam agent, mold release agent, polishing material, sealing material, fabric-finishing agent and the like.

Following are examples to illustrate the inventive method in more detail.

EXAMPLE 1

Into a flask of 2 liters capacity equipped with a stirrer were introduced 790 g of water, 10 g of a quaternary ammonium type cationic surface active agent (Ethoquad C-12, a product by Kao Atlas Co.) and 116 g of sodium carbonate and the mixture was agitated well to form a uniform solution. Into the thus formed reaction mixture at room temperature under agitation was added dropwise a mixture of 74.8 g of methyl trichlorosilane and 54.5 g of trimethyl chlorosilane over a period of 4 hours so that a neutral emulsion with stability was obtained which was a dispersion of the organopolysiloxane formed by the hydrolysis of the silanes followed by the condensation.

EXAMPLE 2

The experimental procedure was substantially the same as in the preceding example except that the silane mixture added to the aqueous medium was composed of 74.8 g of methyl trichlorosilane, 32.3 g of dimethyl dichlorosilane and 27.2 g of trimethyl chlorosilane. A neutral aqueous emulsion with stability containing the organopolysiloxane was obtained.

EXAMPLE 3

The experimental procedure was substantially the same as in Example 2 except that the cationic surface active agent was replaced with 10 g of a nonionic surface active agent of the polyoxyethylene nonyl phenyl ether type having an HLB value of 13.3 (Nonion NS-210, a product by Nippon Yushi Co.) and the sodium carbonate was replaced with 132 g of 29% ammonia water. A neutral aqueous emulsion with stability containing the organopolysiloxane was obtained.

EXAMPLE 4

Into a flask of 2 liters capacity equipped with a stirrer were introduced 750 g of water and 50 g of the same cationic surface active agent as used in Example 1 and the mixture was agitated well to form a uniform reaction mixture. Into this reaction mixture at room temperature under agitation were added 149.5 g of methyl trichlorosilane and 180 g of 29% ammonium water each dropwise through a dropping funnel separately over a period of 4 hours at such a uniform rate that addition of each of the silane and ammonia water was completed at about the same time at the end of the 4 hours period. A neutral aqueous emulsion with stability was obtained containing the organopolysiloxane formed from methyl trichlorosilane alone.

EXAMPLE 5

Into a flask of 2 liters capacity equipped with a stirrer were introduced 495 g of water, 5 g of the same nonionic surface active agent as used in Example 3 and 500 ml of a weakly basic, polyamine-type anion exchange resin having an ion exchange capacity of 1.9 m equivalents/ml (Amberlite IRA-45, a product by Rohm & Haas Co.) in the OH-form and the mixture was agitated well. Into the thus formed reaction mixture at room temperature under agitation were added dropwise a mixture of 29.9 g of methyl trichlorosilane, 12.9 g of dimethyl dichlorosilane and 10.9 g of trimethyl chlorosilane over a period of about 2 hours and then the ion exchange resin was removed by filtration from the reaction mixture. A neutral aqueous silicone emulsion with stability was obtained.

EXAMPLE 6

Into a flask of 2 liters capacity equipped with a stirrer were introduced 790 g of water and 10 g of sodium dodecylbenzene sulfonate as an anionic surface active agent (Osen S, a product by Nippon Yushi Co.) and the mixture was agitated well to form a uniform solution. Into the thus formed aqueous solution at room temperature under agitation were added dropwise a mixture of 38.9 g of methyl trichlorosilane, 30.4 g of diphenyl dichlorosilane and 27.9 g of methyl diphenyl chlorosilane over a period of about 2 hours. A stable but strongly acidic aqueous emulsion was obtained containing an organopolysiloxane as a hydrolysis-condensation product of the mixed silanes.

In the next place, the above obtained aqueous silicone emulsion of strong acidity was introduced into a column of 3 liters capactiy with an inner diameter of 10 cm filled with 2.5 liters of a weakly basic, tertiary amine-type anion exchange resin having an ion exchange capacity of 1.2 m equivalents/ml (Amberlite IRA-94, a product by Rohm & Haas Co.) in the OH-form at the column top to flow down through the bed of the ion exchange resin at a linear velocity of 5 cm/minute. The aqueous emulsion discharged out of the column bottom was no longer acidic retaining the stability of the emulsion.

EXAMPLE 7

The aqueous silicone emulsions obtained in Examples 1 to 6 were evaluated for the performance as an antifoam agent, water-repellent agent and mold release agent to give very satisfactory results as shown in Table 1 below. The testing method for each of the above items was as follows.

(1) Antifoam Activity

Into a 200 ml graduated measuring cylinder with a ground glass stopper was taken 40 ml of a 0.2% aqueous solution of sodium oleate and the solution was strongly shaken 20 times to produce foams in the stoppered cylinder. Then, a 0.2 ml portion of the aqueous silicone emulsion under testing was added dropwise on to the foams and the volume of the foam layer after 2 minutes was recorded as a measure of the foam-destroying power. Thereafter, the stoppered cylinder was again shaken 20 times and the foam volume immediately after completion of this shaking was recorded as a measure of the foam-reducing power.

(2) Water Repellency

A slate board of 7 cm×10 cm×10 mm dimensions was coated with the aqueous silicone emulsion under testing by brushing followed by air drying. A small volume of water was dropped on to the thus treated slate board by use of a rubber-capped dropping pipette and the condition of the water drops was visually examined to give the results recorded by the following criteria.

A: excellent; B: good; C: fair; and D: poor (no water-repellency)

(3) Mold Releasability

A plate of fiber-reinforced epoxy resin was coated with the aqueous silicone emulsion under testing by brushing followed by air drying and a prepolymer composition for semi-rigid polyurethane foam prepared with the formulation shown below was spread on the thus coated epoxy resin plate followed by heating at 60° C. for 30 minutes to effect curing of the polyurethane composition. The layer of the thus cured polyurethane composition was peeled off apart from the resin plate and the peeling behavior was recorded to give the results given by the following criteria.

A: very light peeling; B: considerably light peeling; C: slightly resistant to peeling; and D: peeling impossible Formulation of the polyurethane composition (parts by weight)

Polypropyleneglycol polyol (molecular weight 3000): 100.0
Water: 2.0
Tetramethylene diamine: 1.0
80:20 mixture of 2,6- and 2,4-tolylene diisocyanates, index NCO/OH ratio=105: 6.1
Foam stabilizing agent F-120 (Shin-Etsu Chem. Co.): 0.5

TABLE 1

| Example No. | Antifoam activity | | Water-repellency | Mold releasability |
| --- | --- | --- | --- | --- |
| | Foam-destroying power, ml | Foam-reducing power, ml | | |
| 1 | 115 | 100 | A | B |
| 2 | 90 | 75 | A | A |
| 3 | 84 | 68 | B | A |
| 4 | 150 | 105 | A | A |
| 5 | 95 | 80 | A | B |
| 6 | 78 | 60 | B | A |

What is claimed is:

1. A method for the preparation of an aqueous emulsion of silicone which comprises the steps of:
   (a) adding an organochlorosilane or a mixture of organochlorosilanes each expressed by the general formula $R_nSiCl_{4-n}$, in which R is a hydrogen atom or a halogen-substituted or unsubstituted monovalent hydrocarbon group having from 1 to 20 carbon atoms, at least one of the groups R being not a hydrogen atom, and n is a number of 1, 2 or 3, dropwise into an aqueous medium in the presence of a surface active agent under agitation to effect the hydrolysis of the silane or silanes following by the dehydration condensation of the resultant organosilanols into an organopolysiloxane with simultaneous emulsification of the organopolysiloxane in the aqueous medium to form an aqueous emulsion, and
   (b) removing the hydrogen chloride formed by the hydrolysis of the silane or silanes from the aqueous emulsion by use of a neutralizing agent.

2. The method as claimed in claim 1 wherein the step (b) is performed subsequent to the step (a).

3. The method as claimed in claim 1 wherein the step (b) is performed concurrently with the step (a) by adding the neutralizing agent to the aqueous medium prior to the step (a) or along with the addition of the organochlorosilane or a mixture of organochlorosilanes to the aqueous medium.

4. The method as claimed in claim 1 wherein the step (b) is performed by adding the neutralizing agent to the aqueous medium.

5. The method as claimed in claim 1 wherein the neutralizing agent is a basic or alkaline substance.

6. The method as claimed in claim 1 wherein the step (b) is performed by contacting the aqueous medium with an ion exchange resin as a neutralizing agent.

7. The method as claimed in claim 1 wherein the surface active agent is dissolved in advance in the aqueous medium.

8. The method as claimed in claim 6 wherein the ion exchange resin is a weakly basic anion exchange resin in the OH-form.

9. The method as claimed in claim 1 wherein the surface active agent has an HLB value in the range from 5 to 20.

10. The method as claimed in claim 7 wherein the amount of the surface active agent is in the range from 1/1000 to 1/5 by weight of the water in the aqueous medium.

11. The method as claimed in claim 1 wherein the step (a) is performed at a temperature in the range from 5° to 80° C.

* * * * *